(12) United States Patent
Wang et al.

(10) Patent No.: US 12,733,975 B2
(45) Date of Patent: Sep. 15, 2026

(54) DETECTION MECHANISM, RADIO-FREQUENCY ABLATION CATHETER AND RADIO-FREQUENCY ABLATION SYSTEM

(71) Applicant: HANGZHOU BRONCUS MEDICAL CO., LTD., Hangzhou (CN)

(72) Inventors: Liming Wang, Hangzhou (CN); Hong Xu, Hangzhou (CN); Huazhen Zhou, Hangzhou (CN)

(73) Assignee: Hangzhou Broncus Medical Co., Ltd., Hangzhou (CN)

( * ) Notice: Subject to any disclaimer, the term of this patent is extended or adjusted under 35 U.S.C. 154(b) by 993 days.

(21) Appl. No.: 17/853,474

(22) Filed: Jun. 29, 2022

(65) Prior Publication Data

US 2022/0323149 A1 Oct. 13, 2022

Related U.S. Application Data

(63) Continuation of application No. PCT/CN2020/118646, filed on Sep. 29, 2020.

(30) Foreign Application Priority Data

Dec. 31, 2019 (CN) ......................... 201911403441.5

(51) Int. Cl.
*A61B 18/14* (2006.01)
*A61B 18/00* (2006.01)

(52) U.S. Cl.
CPC ...... *A61B 18/1492* (2013.01); *A61B 18/1477* (2013.01); *A61B 2018/00083* (2013.01);
(Continued)

(58) Field of Classification Search
None
See application file for complete search history.

(56) References Cited

U.S. PATENT DOCUMENTS 9,675,404 B2 6/2017 Shikhman et al.
2011/0202053 A1 8/2011 Moss et al.
(Continued)

FOREIGN PATENT DOCUMENTS

CN 1147964 A 4/1997
CN 2855351 Y 1/2007
(Continued)

OTHER PUBLICATIONS

Japanese Office Action in corresponding Japanese Application No. 2022-540624, dated Jul. 11, 2023.
(Continued)

*Primary Examiner* — Joanne M Rodden
*Assistant Examiner* — Nora W Rhodes

(57) ABSTRACT

Disclosed are a detection mechanism, a radio-frequency ablation catheter, and a radio-frequency ablation system. The radio-frequency ablation catheter includes a handle portion, a needle tube portion, a central electrode, and a detection mechanism. The needle tube portion includes a first tube and a second tube, the handle portion includes a cylinder sleeve and a sliding button, the central electrode includes an electrode body, an electrode wire, and an electrode connector, and the detection mechanism includes a fixing base, a pulling string, a connecting base, and multiple detection electrodes arranged in a claw-shaped configuration. A distal end of the pulling string is fixed to the fixing base, and a proximal end of the pulling string is fixed to the sliding button; and the detection electrodes are fixed to the fixing base, and slidably provided in the connecting base.

21 Claims, 6 Drawing Sheets

(52) U.S. Cl.
CPC ............... *A61B 2018/00101* (2013.01); *A61B 2018/00577* (2013.01); *A61B 2018/00791* (2013.01); *A61B 2018/1405* (2013.01); *A61B 2218/002* (2013.01)

(56) References Cited

U.S. PATENT DOCUMENTS

| | | | | |
|---|---|---|---|---|
| 2014/0276759 | A1* | 9/2014 | Kim | A61B 18/1492 606/33 |
| 2015/0238247 | A1* | 8/2015 | Shikhman | A61B 18/14 606/41 |
| 2016/0120585 | A1* | 5/2016 | Poulsen | A61B 18/04 606/31 |
| 2019/0111236 | A1* | 4/2019 | Oliverius | A61M 25/0136 |
| 2019/0336729 | A1* | 11/2019 | Curley | A61B 18/1477 |
| 2020/0129086 | A1* | 4/2020 | Ganapathy | A61B 5/0538 |

FOREIGN PATENT DOCUMENTS

| | | | |
|---|---|---|---|
| CN | 105434040 | A | 3/2016 |
| CN | 110074860 | A | 8/2019 |
| JP | H1024049 | A | 1/1998 |
| WO | 2007005830 | A2 | 1/2007 |

OTHER PUBLICATIONS

International Search Report in corresponding International Application No. PCT/CN2020/118646, mailed Dec. 30, 2020.
The Extended European Search Report Issued on Jan. 18, 2024 for Corresponding European Patent Application No. 20909204.8.

* cited by examiner

DETECTION MECHANISM, RADIO-FREQUENCY ABLATION CATHETER AND RADIO-FREQUENCY ABLATION SYSTEM

CROSS REFERENCE OF RELATED APPLICATIONS

This application is a continuation of International Patent Application No. PCT/CN2020/118646, filed on Sep. 29, 2020, which claims the priority of Chinese Patent Application No. 201911403441.5, filed on Dec. 31, 2019, the entire contents of which are hereby incorporated by reference in their entities.

TECHNICAL FIELD

The present disclosure relates to the technical field of medical instruments, and in particular to a detection mechanism, a radio-frequency ablation catheter, and a radio-frequency ablation system.

BACKGROUND

The radio-frequency (RF) ablation technology is widely used in lung surgeries. RF refers to radio frequency, but does not belong to divided bands in radio communication. A main function of RF on organisms is a thermal effect. When a current frequency of the RF reaches a certain value (greater than 100 kHz), charged ions within a tissue will move and thus heat (60° C. to 100° C.) is generated by friction. A frequency commonly used by a radio-frequency ablation device ranges 200 kHz to 500 kHz and an output power thereof ranges from 100 kHz to 400 kHz. An ablation electrode is a core component of a radio-frequency ablation system, because it directly affects a size and a shape of coagulation necrosis. An ideal shape of a coagulation region should be spherical or oblate-sphere. Under the guidance of B-ultrasound or CT, a multi-needle electrode is directly punctured into a tumor tissue. A radio-frequency electrode needle may cause a temperature within the tissue to exceed 60° C. which results in cell death and a necrosis region. If a local temperature of the tissue exceeds 100° C., the coagulation necrosis will occur in a tumor tissue and parenchyma surrounding the organ, and a large spherical coagulation necrosis region may be produced during treatment. A hyperthermia region of 43° C. to 60° C. exists outside the coagulation necrosis region. In this region, cancer cells can be killed while normal cells can be restored.

In a treatment process, the radio-frequency electrode is delivered into a human tissue, and a current is introduced into a lesion through the radio-frequency electrode, resulting in a large amount of heat at the radio-frequency electrode. For example, when a temperature at the lesion reaches 40° C. to 60° C. and remains for a period of time, the ablation surgery at the lesion is completed. However, in a radio-frequency ablation system of the prior art, it cannot determine working state information of the radio-frequency electrode, such as a temperature near the radio-frequency electrode. Therefore, in a surgical process, the progress of the ablation surgery can only be determined and adjusted only based on doctor's experiences, which increases the surgical difficulty and accuracy. Accordingly, how to provide a radio-frequency ablation system to accurately determine whether ablation is completed is an urgent problem to be solved in the art.

SUMMARY

An objective of the present disclosure is to provide a detection mechanism, a radio-frequency ablation catheter, and a radio-frequency ablation system. During the radio-frequency ablation process, the expansion and retraction of the detection electrodes can be controlled by pushing a sliding button on a handle to move back and forth. This achieves not only the auxiliary positioning of an electrode body, but also the determination of the situation around the electrode body by the detection electrodes.

An embodiment of the present disclosure provides a detection mechanism for a radio-frequency ablation catheter, which includes a fixing base, a pulling string, a connecting base and a plurality of detection electrodes arranged in a claw-shaped configuration, wherein the fixing base is configured to be slidably mounted in the radio-frequency ablation catheter;

the fixing base is provided with a plurality of mounting holes, and each of the detection electrodes extends through a respective mounting hole and is fixedly connected to the fixing base;

a distal end of the pulling string is fixed to the fixing base, and a proximal end of the pulling string is configured to be connected to the sliding button of the radio-frequency ablation catheter;

the connecting base is configured to be fixedly mounted in the radio-frequency ablation catheter;

the connecting base is provided with a plurality of guide holes, wherein openings of adjacent guide holes extend in a same direction, each detection electrode extends through a respective guide hole, and the guide holes allow the detection electrodes to extend out of the connecting base in a dispersed manner; and each detection electrode includes: a first section, a second section, and a third section, wherein an included angle between the second section and the first section is an obtuse angle, and an included angle between the third section and the second section is an obtuse angle, wherein when the detection electrodes extend out of the connecting base in a separate manner, the detection electrodes are unfolded, and distal ends of the detection electrodes are located on a same latitude.

An embodiment of the present disclosure provides a radio-frequency ablation catheter, including a handle portion, a needle tube portion, a central electrode, and any one of above detection mechanisms, wherein the needle tube portion includes a first tube and a second tube, wherein the connecting base is mounted between the first tube and the second tube, the fixing base is slidably mounted in the first tube, and the plurality of fixing rings and the plurality of detection electrodes are located inside the first tube;

the handle portion includes a cylinder sleeve and a sliding button, wherein the sliding button is slidably mounted on the cylinder sleeve, and a proximal end of the pulling string is fixed to the sliding button; and the central electrode includes an electrode body, an electrode wire, and an electrode connector, wherein the electrode body is provided at a distal end of the second tube, a distal end of the electrode wire is electrically connected to the electrode body, the electrode wire extends through the cylinder sleeve, the first tube and the second tube, a proximal end of the electrode wire is electrically connected to the electrode connector, and the electrode connector is located outside the cylinder sleeve.

An embodiment of the present disclosure also provides a radio-frequency ablation system, which includes the radio-frequency ablation catheter described in any one of the foregoing feasible embodiments.

Based on the above embodiments, it can be known that the detection mechanism, the radio-frequency ablation catheter, and the radio-frequency ablation system according to the present disclosure include a handle portion, a needle tube portion, a central electrode, and a detection mechanism. The needle tube portion includes a first tube and a second tube, the handle portion includes a cylinder sleeve and a sliding button, the central electrode includes an electrode body, an electrode wire, and an electrode connector, and the detection mechanism includes a fixing ring, a fixing base, a pulling string, a connecting base, and a plurality of detection electrodes. For the detection mechanism, the radio-frequency ablation catheter, and the radio-frequency ablation system of the present disclosure, take a user as a reference, the end close to the user is the proximal end and the end away from the user is the distal end. The connecting base is mounted between the first tube and the second tube, and the fixing base is located at a proximal end of the connecting base. The fixing base, the fixing ring and the multiple detection electrodes are all provided in the first tube. The fixing base can slide in the first tube, the fixing rings are mounted at a proximal end of the fixing base and fixed to the detection electrodes, and the detection electrodes extend in the fixing base. The detection electrodes can slide in the connecting base, and when the detection electrodes extend out of the connecting base, the detection electrodes are arranged in an expansion manner, and are located on the same latitude. The sliding button can slide on the surface of the cylinder sleeve, a proximal end of the pulling string is fixed on the sliding button; and a distal end of the pulling string is fixed to the fixing base. The electrode body is located at a distal end of the second tube, a distal end of the electrode wire is fixed in the electrode body and electrically connected thereto, a proximal end of the electrode wire is electrically connected to the electrode connector, and the electrode connector is located outside the cylinder sleeve. The detection electrodes can be pushed in and pushed out of the needle tube portion by means of the connecting base, the fixing base, and the pulling string. When the detection electrodes need to be pushed out of the needle tube portion for detection, the sliding button is pushed distally, so that the sliding button drives the pulling string to move distally, which in turn drives the fixing base to move distally. At this time, the detection electrodes fixed to the fixing base move distally as the fixing base moves distally. As a result, the detection electrodes previously received in the connecting base are pushed out of the needle tube portion. When there is no need to use the detection electrodes for detection, the sliding button is pushed proximally, so that the sliding button drives the pulling string to move proximally, which in turn drives the fixing base to move proximally, so as to pull the detection electrodes back. At this time, the detection electrodes previously located outside the needle tube portion are retracted inside the connecting base again. By means of the sliding button, the pulling string and the fixing base are driven to move to finally achieve the push-out and retraction of the detection electrodes. This facilitates the control of the detection electrodes by a user during the surgery. During the radio-frequency ablation process, the expansion and retraction of the detection electrodes can be controlled by pushing the sliding button on the handle to move back and forth. This achieves not only the auxiliary positioning of an electrode body, but also the determination of the situation around the electrode body by the detection electrodes, and thus the determination of the progress of ablation.

BRIEF DESCRIPTION OF THE DRAWINGS

In order to describe the technical solutions according to the embodiments of the present disclosure or in the prior art more clearly, the drawings needed to be used in the embodiments or in the prior art will be described briefly below. Apparently, the drawings in the following description show some embodiments of the present application. Other drawings can be obtained by persons of ordinary skill in the art based on these drawings without creative efforts.

REFERENCE NUMERALS

Figure 1:
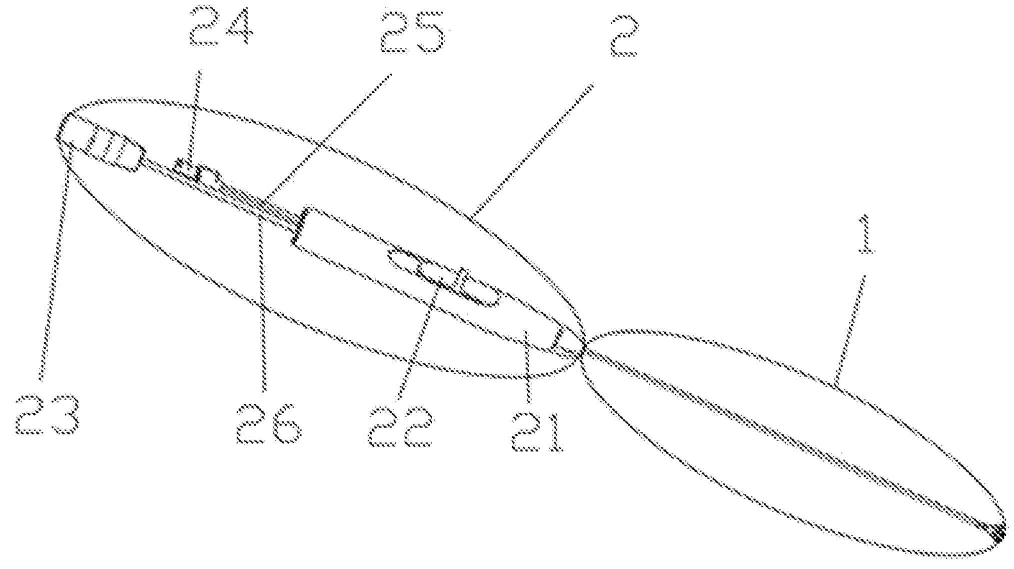
FIG. 1 is a schematic view showing the overall structure of a radio-frequency ablation catheter according to a first embodiment of the present disclosure.

1. needle tube portion; 11. first tube; 111. counterbore; 12. second tube; 121. internal thread; 2. handle portion; 21. cylinder sleeve; 22. sliding button; 23. electrode connector; 24. liquid injection joint; 25. liquid injection tube; 26. electrode wire; 3. central electrode; 301. signal conduit; 31. electrode body; 311. liquid inlet; 312. sprinkler channel; 32. infiltration cover; 321. dispersing hole; 33. temperature sensor; 34. wiring hole; 35. engaging groove; 4. fixing ring; 41. slit; 42. buffering cushion; 5. fixing base; 501. pulling string; 51. mounting holes; 52. through hole; 53. first groove; 54. fixture block; 55. male fixing base; 551. protrusion; 56. female fixing base 561. second groove; 57. hinge shaft; 6. connecting base; 61. guide hole; 611. straight section; 6111. anti-slid pattern; 612. curved section; 6121. anti-wear pad; 62. liquid injection hole; 63. external thread; 64. threaded hole; 65. mounting hole; 7. detection electrode; 71. first section; 72. second section; 73. third section; 8. spring; 9. insulating layer.

DESCRIPTION OF THE EMBODIMENTS

In order to make the objects, technical solutions and advantages of the embodiments of the present disclosure clearer, the technical solutions according to the embodiments of the present disclosure will be clearly and completely described with reference to drawings in the embodiments of the present disclosure. Apparently, the embodiments described are merely some embodiments, but not all of the embodiments of the present application. All other embodiments obtained by ordinary persons skilled in the art based on the embodiments of the present disclosure without creative efforts shall fall within the protection scope of the present disclosure.

In the description of the present disclosure, it should be understood that the terms "center", "longitudinal", "transverse", "upper", "lower", "front", "rear", "left", "right", "vertical", "horizontal", "top", "bottom", "inner", "outer", "axial", "radial", "circumferential" and others indicate directional or position relations based on orientations or position relationships shown in the accompanying drawings, only for the convenience of describing the present disclosure and simplifying the description, rather than indicating or implying that the device or element referred to must have a specific orientation, and be constructed and operated in a specific orientation. Therefore, these terms cannot be understood as limitations of the present disclosure.

In the present disclosure, unless otherwise clearly specified and limited, the terms "mounted", "connected with", "connected", "fixed" and others should be understood in a broad sense. For example, the connection may be fixed connection or detachable connection, or forms a one-piece structure; may be mechanical connection, electrical connection, or communication connection; may be direct connection, or indirect connection via an intermediate structure; or may be communication inside two elements or interaction relationship between two elements, unless otherwise clearly defined. For those of ordinary skill in the art, specific meanings of the above terms in the present disclosure can be understood according to specific circumstances. Hereinafter, the technical solutions of the present disclosure will be described in detail below in connection with specific embodiments. The following specific embodiments can be combined with each other, in which the same or similar concepts or processes may not be repeated in some embodiments.

Figure 2:
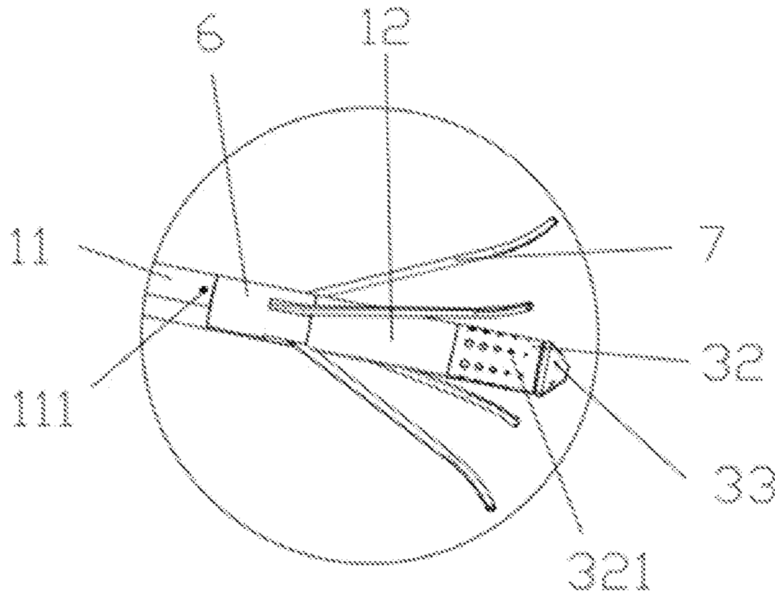
FIG. 2 is a partially enlarged view of a needle tube portion of the radio-frequency ablation catheter according to the first embodiment of the present disclosure.
Figure 3:
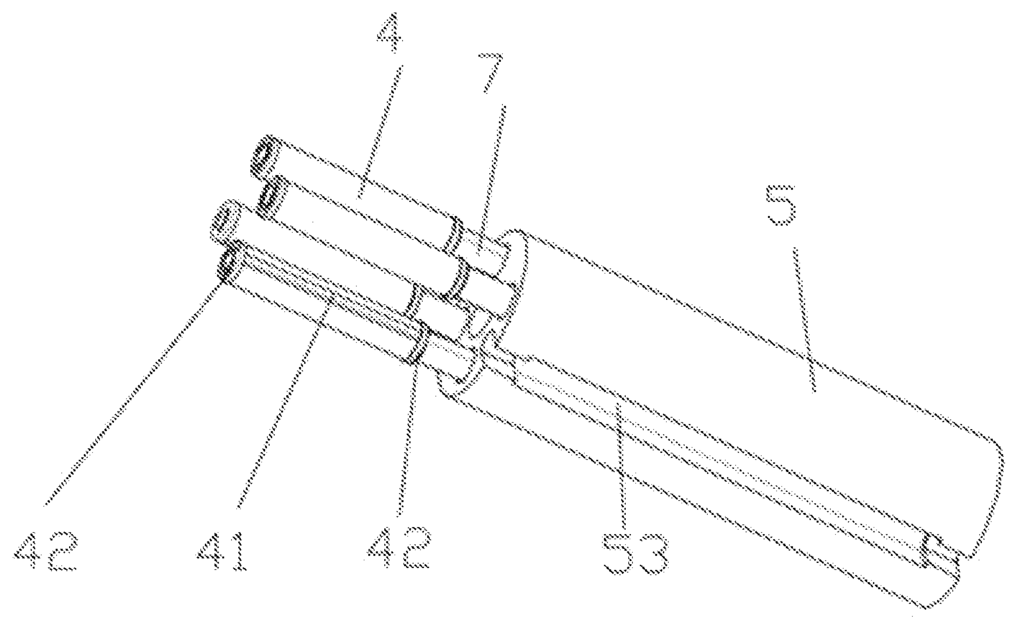
FIG. 3 shows a fixing base connected to fixing rings of the radio-frequency ablation catheter according to the first embodiment of the present disclosure.
Figure 4:
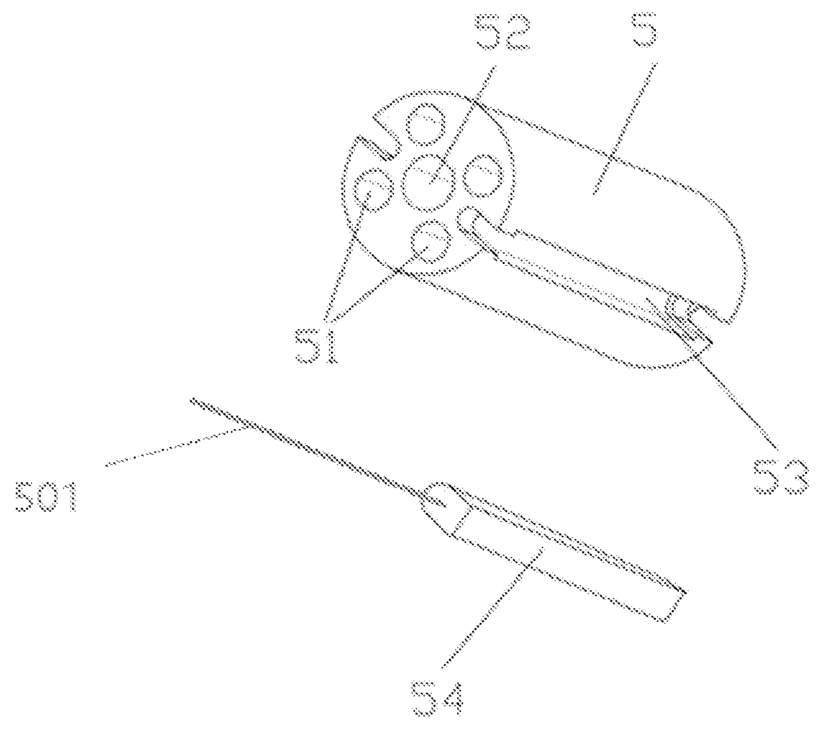
FIG. 4 is a schematic structural view of the fixing base of the radio-frequency ablation catheter according to the first embodiment of the present disclosure.
Figure 5:
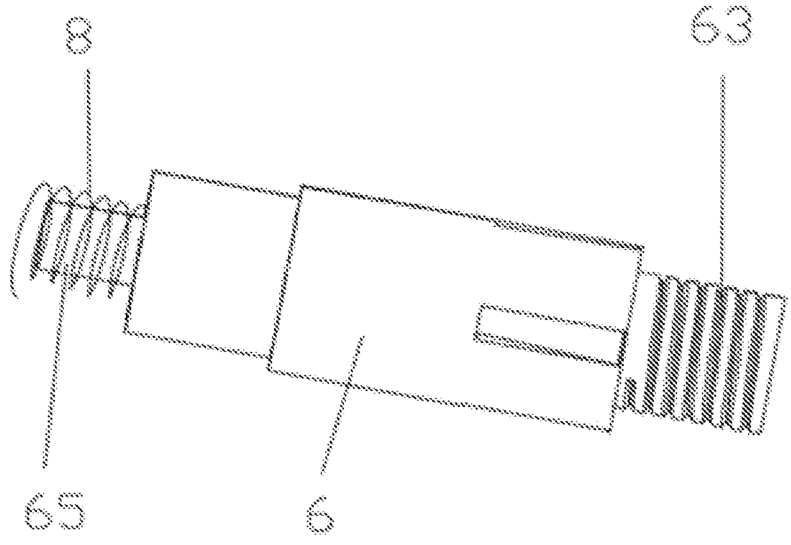
FIG. 5 is a schematic view showing the positions of the connecting base and a spring of the radio-frequency ablation catheter according to the first embodiment of the present disclosure.
Figure 6:
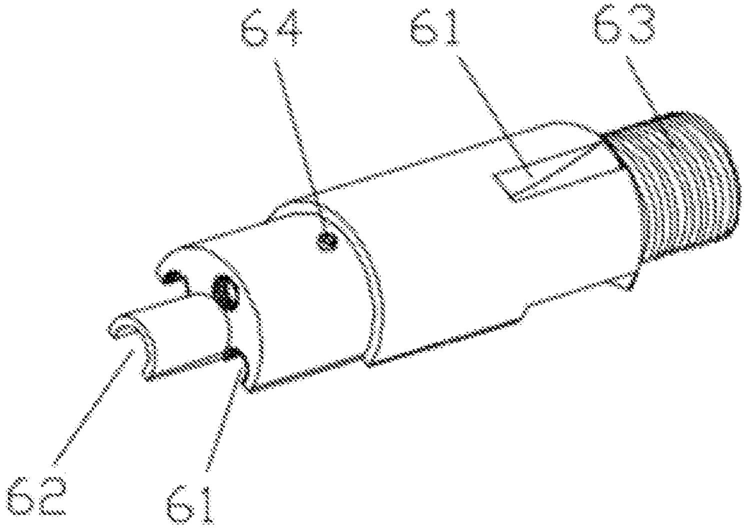
FIG. 6 is a first sectional view of the connecting base of the radio-frequency ablation catheter according to the first embodiment of the present disclosure.
Figure 7:
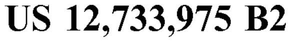
FIG. 7 is a second sectional view of the connecting base of the radio-frequency ablation catheter according to the first embodiment of the present disclosure.
Figure 7:
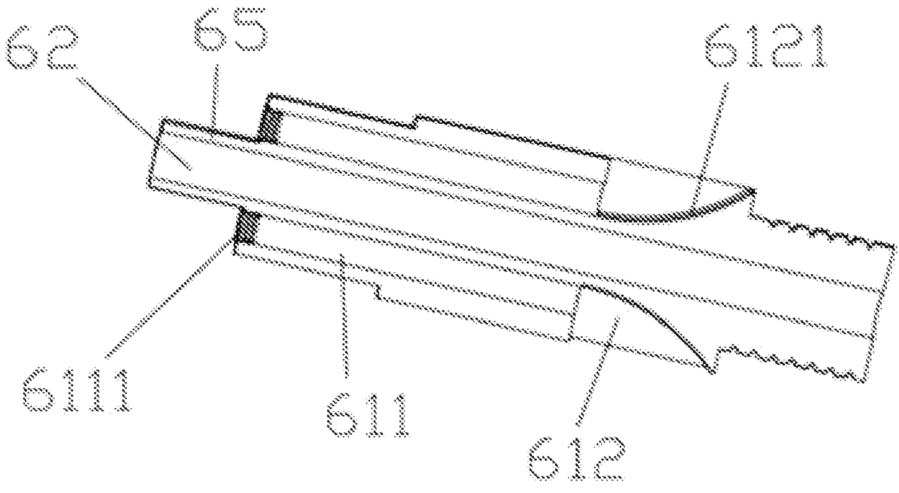
Figure 8:
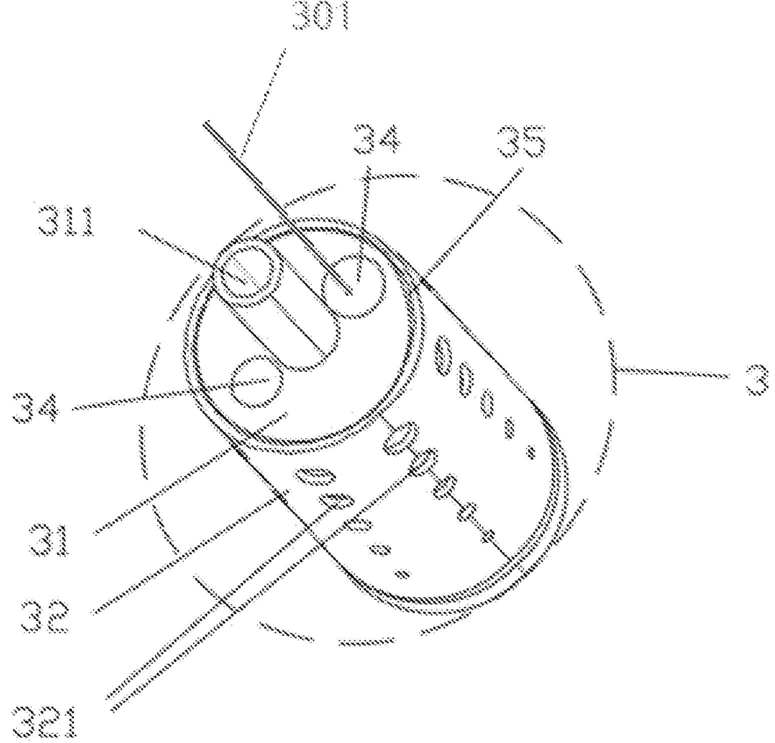
FIG. 8 is a schematic view showing the overall structure of an infiltration cover of the radio-frequency ablation catheter according to the first embodiment of the present disclosure.
Figure 9:
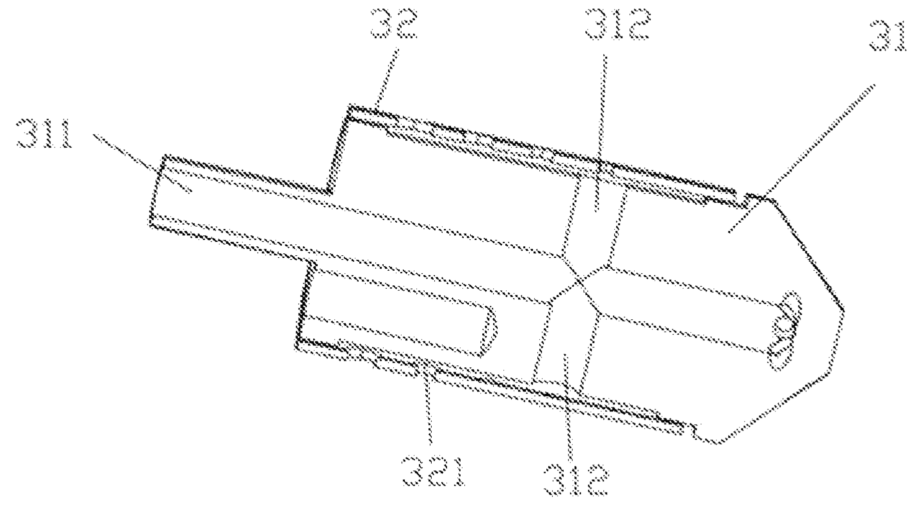
FIG. 9 is a sectional view of the infiltration cover of the radio-frequency ablation catheter according to the first embodiment of the present disclosure.
Figure 10:
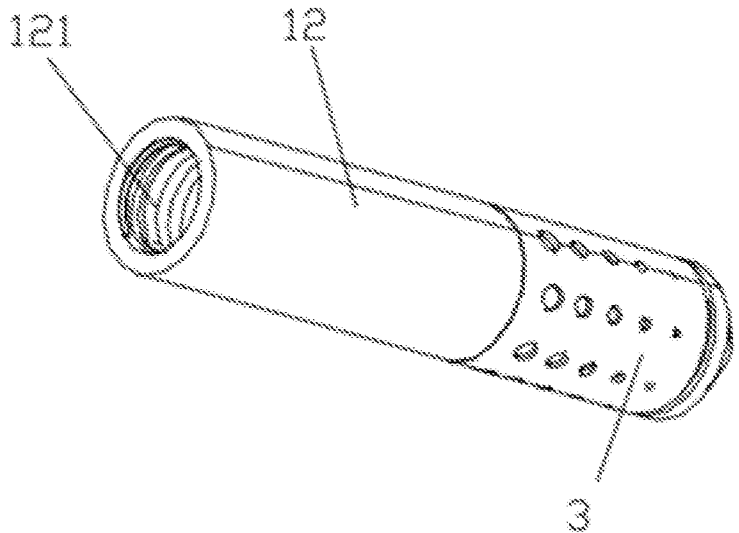
FIG. 10 is a schematic view showing a second tube connected to the infiltration cover of the radio-frequency ablation catheter according to the first embodiment of the present disclosure.
Figure 11:
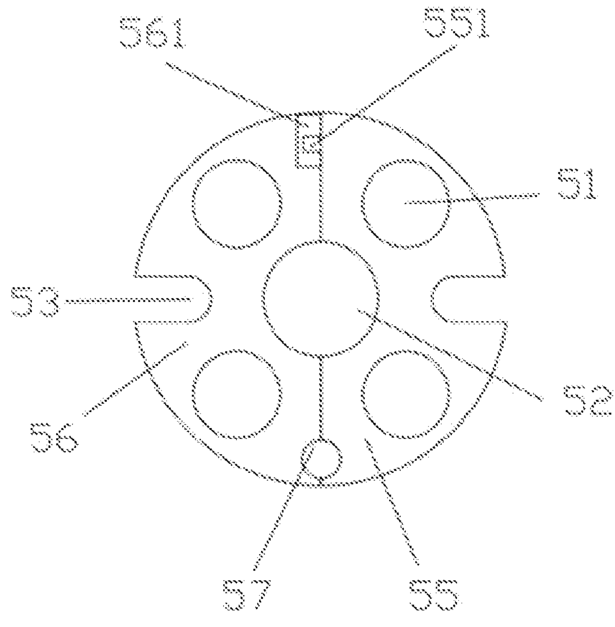
FIG. 11 is a left side view of the fixing base of the radio-frequency ablation catheter according to the first embodiment of the present disclosure.

FIG. 1 is a schematic view showing the overall structure of a radio-frequency ablation catheter according to a first embodiment of the present disclosure; FIG. 2 is a partially enlarged view of a needle tube portion of the radio-frequency ablation catheter according to the first embodiment of the present disclosure; FIG. 3 shows a fixing base connected to fixing rings of the radio-frequency ablation catheter according to the first embodiment of the present disclosure; FIG. 4 is a schematic structural view of the fixing base of the radio-frequency ablation catheter according to the first embodiment of the present disclosure; FIG. 5 is a schematic view showing the positions of the connecting base and a spring of the radio-frequency ablation catheter according to the first embodiment of the present disclosure; FIG. 6 is a first sectional view of the connecting base of the radio-frequency ablation catheter according to the first embodiment of the present disclosure; FIG. 7 is a second sectional view of the connecting base of the radio-frequency ablation catheter according to the first embodiment of the present disclosure; FIG. 8 is a schematic view showing the overall structure of an infiltration cover of the radio-frequency ablation catheter according to the first embodiment of the present disclosure; FIG. 9 is a sectional view of the infiltration cover of the radio-frequency ablation catheter according to the first embodiment of the present disclosure; FIG. 10 is a schematic view showing a second tube connected to the infiltration cover of the radio-frequency ablation catheter according to the first embodiment of the present disclosure; FIG. 11 is a left side view of the fixing base of the radio-frequency ablation catheter according to the first embodiment of the present disclosure; and FIG. 12 is a schematic structural view of an detection electrode of the radio-frequency ablation catheter according to the first embodiment of the present disclosure.

As shown in FIG. 1, a radio-frequency ablation catheter according to the embodiment includes a handle portion 2, a needle tube portion 1, a central electrode 3 and a detection mechanism. The needle tube portion 1 includes a first tube 11 and a second tube 12. The handle portion 2 includes a cylinder sleeve 21 and a sliding button 22. The central electrode 3 includes an electrode body 31, an electrode wire 26, and an electrode connector 23. The detection mechanism includes fixing rings 4, a fixing base 5, a pulling string 501, a connecting base 6, and a plurality of detection electrodes 7 arranged in a claw-shaped configuration. Take a user as reference, the end close to the user is the proximal end and the end away from the user is the distal end. The radio-frequency ablation catheter includes, from a proximal end to a distal end, the cylinder sleeve 21, the first tube 11, the fixing rings 4, the fixing base 5, the connecting ring 6, the second tube 12, and the central electrode 3 in sequence. The cylinder sleeve 21 is located at a proximal end of the needle tube portion 1, the first tube 11 is mounted around a distal end of the cylinder sleeve 21. The electrode connector 23 is located at a proximal end of the cylinder sleeve 21. A proximal end of the electrode wire 26 is electrically connected to the electrode connector 23, and a distal end of the electrode wire 26 is inserted into and electrically connect to the electrode body 31. The electrode body 31 is located at a distal end of the needle tube portion 1, and fixed at a distal end of the second tube 12. The electrode body 31 is made of fibers. The electrode wire 26 extends through the cylinder sleeve 21, the first tube 11, the fixing base 5, the connecting base 6, the second tube 12 and the electrode body 31, respectively.

Figure 12:
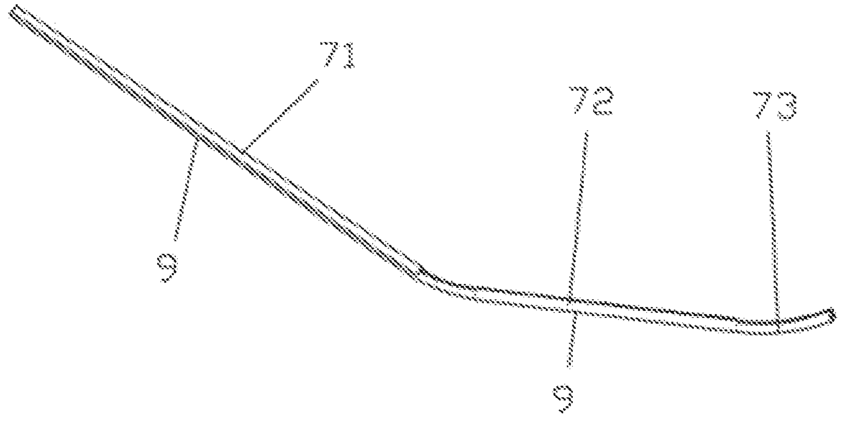
FIG. 12 is a schematic structural view of an detection electrode of the radio-frequency ablation catheter according to the first embodiment of the present disclosure.

As shown in FIG. 12, the detection electrode 7 includes a first section 71, a second section 72, and a third section 73. The first section 71 is a proximal section, the second section 72 is a middle section, and the third section 73 is a distal section. An obtuse angle is formed between the first section 71 and the second section 72, and an obtuse angle is formed between the second section 72 and the third section 73. The detection electrode can obtain an impedance value of a contact position, or the detection electrode itself is made of a heat-sensitive material, to obtain the highest temperature around the detection electrode. In other words, by means of the detection electrode, the detection mechanism can detect the temperature or impedance at the detection electrode, and thus determine the progress of ablation.

As shown in FIG. 4, the fixing base 5 is located in the first tube 11, and the fixing base 5 can slide in the first tube 11. Four mounting holes 51 are provided on the fixing base 5, and the four mounting holes 51 are used to fix the detection electrodes 7. Optionally, the detection electrode 7 is fixed in the mounting hole 51 by dispensing. That is, the detection electrode 7 is fixedly provided in the mounting hole 51 by an adhesive. Alternatively, the detection electrode 7 is fixed in the mounting hole 51 by welding. That is, the detection electrode 7 is welded to the mounting hole 51. A through hole 52 is provided along the central axis of the fixing base 5, and the four mounting holes 51 are symmetrically distributed with the through hole 52 as the center. The through hole 52 is provided for accommodating a signal conduit 301 and a liquid injection tube 25. The pulling string 501 is fixed at a distal end of the fixing base 5.

As shown in FIG. 3, the fixing rings 4 are located in the first tube 11, and located at a proximal end of the fixing base 5. A distal end of the fixing ring 4 is fixedly on the detection electrode 7, and a proximal end of the fixing ring 4 is used to fix an external wire, and allows the wire and the detection electrode to be electrically connected. The external wire extends through the cylinder sleeve 21 and the first tube 11, a proximal end of the external wire is fixed to the electrode connector 23, and a distal end of the external wire is fixed to the fixing ring 4. The first section 71 of the detection electrode 7 extends out of the fixing base 5, and enter the inside of the fixing ring 4. The distal end of the external wire enters the inside of the fixing ring 4 from a proximal end of the fixing ring 4. In the fixing ring 4, the first section 71 of the detection electrode 7 is in contact with the distal end of the external wire, to establish an electrical connection. The electrode connector 23 is externally connected to a radio-frequency ablation system. A current is supplied to the detection electrode 7 through the external wire, and then the current is released into the human tissue by the detection electrode 7. The sliding button 22 is mounted on the surface of the cylinder sleeve 21, and the sliding button 22 can slide on the surface of the cylinder sleeve 21. A distal end of the pulling string 501 is fixed to the fixing base 5, and a proximal end of the pulling string 501 is fixed to the sliding button 22. By pushing the sliding button 22 to move forward or backward, the pulling string 501 is driven to move forward or backward. Since one end of the pulling string 501 is fixed to the fixing base 5, the pulling string 501 drives the fixing base 5 to slide in the first tube 11. The detection electrode 7 is fixed in the fixing base 5. As the fixing base 5 slides forward or backward, the detection electrode 7 fixed in the fixing base 5 will also move forward or backward with the fixing base 5. Optionally, the detection electrode 7 is fixedly connected to the fixing base 5 by adhesive, and they move as a whole.

As shown in FIG. 7, the connecting base 6 is located between the first tube 11 and the second tube 12, and the first tube 11 and the second tube 12 are respectively fixed at a proximal and a distal end of the connecting base 6. Four guide holes 61 are provided on the connecting base 6, and the openings of each two adjacent guide holes 61 extend in same direction. The four guide holes 61 are respectively located in four directions on the connecting base 6, and the four guide holes 61 are circumferentially distributed in array centered on the central axis of the connecting base 6. Therefore, among the four guide holes 61, the distances between each two adjacent guide holes 61 are the same; and the distances between each pair of opposing guide holes 61 are different. The detection electrodes 7 slide through the guide holes 61 in the connecting base 6, and these guide holes 61 enable the detection electrodes 7 to extend out of the connecting base 6 in a separate manner. The four detection electrodes 7 are independent from each other and do not interfere with each other. Since the detection electrode 7 is divided into the first section 71, the second section 72 and the third section 73, when the detection electrode 7 extends out of the connecting base 6, the first section 71 is still located inside the guide hole 61, and the second section 72 and the third section 73 extend out of the guide hole 61 of the connecting base 6 under the pushing force of the fixing base 5, Because of the obtuse angles between the first section 71 and the second section 72, and between the second section 72 and the third section 73, the detection electrodes 7 are arranged radially when they extend out of the connecting base 6, and lengths of the detection electrodes 7 extending out of the needle tube portion 1 are the same. Since the positions of the four guide holes 61 in the connecting base 6 are aligned to each other and the positions of the distal openings of the guide holes 61 are the same relative to the connecting base 6, when the detection electrodes 7 extend out of the guide holes 61, the distal ends of the detection electrodes 7 are at the same latitude.

The radio-frequency ablation catheter is used in a radio-frequency ablation system. The radio-frequency ablation system includes a radio-frequency generator (ablation instrument), wherein the radio-frequency generator (ablation instrument) is used to be connected to the radio-frequency ablation catheter, and provides an electrical signal to the electrode connector of the radio-frequency ablation catheter, to allow the central electrode and the detection electrode to work.

In view of the foregoing description, it can be easily found that the radio-frequency ablation catheter of the present disclosure includes a handle portion 2, a needle tube portion 1, a central electrode 3, and a detection mechanism. The needle tube portion 1 includes a first tube 11 and a second tube 12. The handle portion 2 includes a cylinder sleeve 21 and a sliding button 22. The central electrode 3 includes an electrode body 31, an electrode wire 26, and an electrode connector 23. The detection mechanism includes a fixing ring 4, a fixing base 5, a pulling string 501, a connecting base 6, and a plurality of detection electrodes 7. For the detection mechanism, radio-frequency ablation catheter, and radio-frequency ablation system of the present disclosure, take a user as a reference, the end close to the user is the proximal end and the end away from the user is the distal end. The connecting base 6 is mounted between the first tube 11 and the second tube 12, and the fixing base 5 is located at a proximal end of the connecting base 6. The fixing base 5, the fixing ring 4 and the plurality of detection electrodes 7 are all provided in the first tube 11. The fixing base 5 can slide in the first tube 11, the fixing ring 4 is mounted at a proximal end of the fixing base 5 and fixed to the detection electrode 7, and the detection electrodes 7 are inserted in the fixing base 5. The detection electrodes 7 can slide in the connecting base 6, and when the detection electrodes 7 extend out of the connecting base 6, the detection electrodes 7 extend radially outwardly, and located are on the same latitude. The sliding button 22 can slide on the surface of the cylinder sleeve 21. A proximal end of the pulling string 501 is fixed to the sliding button 22, and a distal end of the pulling string 501 is fixed to the fixing base 5. The electrode body 31 is located at a distal end of the second tube 12, a distal end of the electrode wire 26 is fixed in and electrically connected to the electrode body 31, a proximal end of the electrode wire 26 is electrically connected to the electrode connector 23, and the electrode connector 23 is located outside the cylinder sleeve 21. The detection electrodes 7 can be pushed in and pushed out of the needle tube portion 1 by means of the connecting 6, the fixing base 5, and the pulling string 501. When the detection electrode 7 needs to be pushed out of the needle tube portion 1 for detection, the sliding button 22 is pushed distally, so that the sliding button 22 drives the pulling string 501 to move distally, which in turn drives the fixing base 5 to move distally. At this time, the detection electrodes 7 fixed to the fixing base 5 move distally, as the fixing base 5 moves distally. As a result, the detection electrodes 7 previously received in the connecting base 6 are pushed out of the needle tube portion 1. When there is no need to use the detection electrodes 7 for detection, it only requires to push the sliding button 22 proximally, so the sliding button 22 drives the pulling string 501 to move proximally, which in turn drives the fixing base 5 to move proximally, so as to pull the detection electrodes 7 back. At this time, the detection electrodes 7 previously located outside the needle tube portion 1 are retracted inside the connecting base 6 again. By means of the sliding button 22, the pulling string 501 and the fixing base 5 are driven to move, to finally achieve the push-out and retraction of the detection electrodes 7. This facilitates the control of the detection electrodes 7 by a user during the surgery. When this detection device is used during surgery, the needle tube portion is inserted into the human body, for example, into the human trachea, then the detection electrodes are unfolded by using the sliding button, and the detection electrodes prop against the inner wall of human trachea, to stabilize the central electrode. At the same time, the detection electrodes can obtain the temperature or impedance data of the human trachea, so as to obtain the progress of ablation at the central electrode. Therefore, the detection device not only achieves the auxiliary positioning of the electrode body, but also obtains the progress of ablation by determining the temperature or impedance of the detection electrodes by the detection electrodes.

Optionally, in this embodiment, the radio-frequency ablation catheter further includes: a liquid injection joint 24 and a liquid injection tube 25, wherein the liquid injection joint 24 is located at a proximal end of the cylinder sleeve 21, and the liquid injection joint 24 is connected to an external injector. A proximal end of the liquid injection tube 25 is connected to the liquid injection joint 24, and a distal end of the liquid injection tube 25 is inserted into the electrode body 31. The liquid injection tube 25 is inserted in the cylinder sleeve 21, the first tube 11 and the second tube 12, and extends through the cylinder sleeve 21, the fixing base 5 and the connecting base 6 respectively. A liquid inlet 311 is provided on the electrode body 31, wherein the liquid inlet 311 is located at the middle portion of the electrode body 31, and the liquid inlet 311 is connected to a distal end of the liquid injection tube 25. Saline discharged from an injector flows through the liquid injection joint 24, the liquid injection tube 25 and the liquid inlet 311, and finally enters the interior of the electrode body 31.

As shown in FIG. 9, optionally, in this embodiment, the electrode body 31 includes: a cylindrical portion and a tapered portion, wherein the tapered portion is located at a distal end of the cylindrical portion. An infiltration cover 32 is provided outside the electrode body 31. wherein the infiltration cover 32 is made of high-temperature resistant insulating material, and the infiltration cover 32 is mounted around the cylindrical portion of the electrode body 31. Sprinkler channels 312 are provided inside the electrode body 31, and two pairs of sprinkler channels 312 are distributed in a cross shape. The two pairs of sprinkler channels are communicated with the liquid inlet 311. Saline flowing through the liquid injection tube 25 is gathered in the liquid inlet 311 and then dispensed into the sprinkler channels 312. On the surface of the infiltration cover 32, multiple dispersing holes 321 are provided in a rectangular array, and the diameters of each row of dispersing holes 321 decrease in a direction from the proximal end to the distal end. The dispersing holes 321 are in communication with the sprinkler channels 312, and arranged misaligned with the sprinkler channels 312. There is a gap between the infiltration cover 32 and the surface of the electrode body 31, and the saline in the sprinkler channel 312 flows through the gap to the infiltration cover 32. Due to the multiple dispersing holes 321 formed on the surface of the infiltration cover 32, the saline flows out through the dispersing holes 321, to diffuse inside the body tissue.

Optionally, in this embodiment, the electrode body 31 is further provided with a temperature sensor 33 and a signal conduit 301 therein. A wiring hole 34 is provided in the electrode body 31, and the wiring hole 34 is located on a side where the liquid inlet 311 is located. The signal conduit 301 is inserted into the wiring hole 34. The temperature sensor 33 is located on the surface of the tapered portion of the electrode body 31. The temperature sensor 33 is electrically connected to a distal end of the signal conduit 301, and a proximal end of the signal conduit 301 is fixed to and electrically connected to the electrode connector 23. A rubber insulating layer 9 is provided outside the signal conduit 301. The temperature sensor 33 may be a thermistor, which is sensitive to temperature, and shows different resistance at different temperatures, wherein the resistance decreases as the temperature increases. After the saline is infiltrated into the human tissue from the dispersing holes 321, the ablation process starts. With the continuous increase of ablation saline and continuous increase of the ablation area, the temperature of the ablation area changes gradually. When the temperature becomes higher and higher, the resistance of the thermistor in a local area decreases as the temperature increases. The thermistor and the signal conduit 301 are electrically connected. When the resistance of the thermistor changes, the resistance change is transmitted to the radio-frequency ablation system by the signal conduit 301. A distal end of the signal conduit 301 is connected to the thermistor, and a proximal end of the signal conduit 301 is fixed to the electrode connector 23. According to the resistance change on the radio-frequency ablation system, the local temperature change of the tissue is calculated. In this way, the temperature can be controlled by the flow rate of the saline. Moreover, the temperature change inside human tissue can be directly observed on the radio-frequency ablation system.

As shown in FIG. 8, optionally, in this embodiment, an engaging groove 35 is provided at a proximal end of the electrode body 31, and an outer wall of the second tube 12 is engaged in the engaging groove 35, to fix the electrode body 31 and the second tube 12 together. The second tube 12 is provided with an internal thread 121 at a proximal end thereof, the connecting base 6 is provided with an external thread 63 at the distal end thereof, and the connecting base 6 and the second tube 12 are threadedly connected.

Optionally, in this embodiment, the connecting base 6 is provided with a threaded hole 64 at the proximal end thereof, the first tube 11 is provided with a counterbore 111 at a distal end thereof, and a bolt is inserted into the counterbore 111 and the threaded hole 64 to fix the connecting base 6 and the first tube 11 together. As the bolt is continuously screwed in, the connecting base 6 and the first tube 11 are fastened. When the bolt is fully screwed into the threaded hole 64, the surface of the bolt is flush with the surface of the connecting base 6, and the bolt is received into the counterbore 111.

Optionally, in this embodiment, a liquid injection hole 62 is provided in the connecting base 6 along the central axis thereof. The liquid injection tube 25 and the signal conduit 301 are inserted in the liquid injection hole 62. The four guide holes 61 on the connecting base 6 are symmetrically distributed with the liquid injection hole 62 as a center. The liquid injection hole 62 is used to define the position of the liquid injection tube 25, preventing the sliding path of the liquid injection tube 25 from deviating. The guide hole 61 includes a straight section 611 and a curved section 612. The straight section 611 is located at a proximal end of the curved section 612. Since the first section 71, the second section 72 and the third section 73 of the detection electrode 7 are connected each other with obtuse angles formed therebetween, the connection between the straight section 611 and the curved section 612 of the guide hole 61 can facilitate sliding of the detection electrode 7. The curved section 612 is convenient for the detection electrode 7 to expand or retract independently and smoothly, to thereby increase the support force and expansion degree of the detection electrode 7. An anti-skid pattern 6111 is provided on an inner side wall of the straight section 611 of the guide hole 61. When the detection electrode 7 extends out of the needle tube portion 1, the anti-skid pattern 6111 in the straight section 611 facilitates fixing the position of the detection electrode 7 to keep it stable. An anti-wear pad 6121 made of a silicone material is provided on the inner side wall of each curved section 612, and the anti-wear pad 6121 is located between the curved section 612 and the detection electrode 7. When the detection electrode 7 is pushed out of or pulled into the connecting base 6, there is a trend to cause a friction between the detection electrode 7 and the surface of the curved section 612 which may damage the surface of the detection electrode 7, the provision of the anti-wear pad 6121 can ameliorate the abrasion on the surface of the detection electrode 7.

As shown in FIG. 5, optionally, in this embodiment, a mounting post 65 is provided at the proximal end of the connecting base 6, and a spring 8 is mounted around the mounting post 65. When the detection electrode 7 extends out of the needle tube portion 1, the fixing base 5 moves towards the connecting base 6. When the fixing base 5 moves towards the connecting base 6, a distal end of the spring 8 abuts against the proximal end of the connecting base 6, and a proximal end of the spring 8 abuts against the fixing base 5. The provision of the spring 8 increases the cushion force when the detection electrode 7 extends out of the connecting base 6, and keep the detection electrode 7 stable. As shown in FIG. 12, optionally, in this embodiment, the detection electrode 7 is hollow, and the surfaces of the first section 71 and the second section 72 of the detection electrode 7 are both provided with an insulating layer 9 made of a rubber material. When a current flows to the detection electrode 7 via a conductive tube, signal interference is caused. The provision of a layer of rubber on the surface of the detection electrode 7 can reduce signal interference, by signal shielding. The first section 71 and the second section 72 of the detection electrode 7 are both straight sections 611, and the third section 73 is a curved section.

As shown in FIG. 4, optionally, in this embodiment, two first grooves 53 are provided on the surface of the fixing base 5, a fixture block 54 is provided at the distal end of the pulling string 501, and the first groove 53 is used to fix the pulling string 501. When the pulling string 501 needs to be engaged into the first groove 53, the fixture block 54 on the pulling string 501 can be directly pushed into the first groove 53, to allow the fixture block 54 on the pulling string 501 to be exactly engaged into the first groove 53. By means of the cooperation of the block 54 and the first groove 53, the pulling string 501 is fixed on the fixing base 5.

As shown in FIG. 11, optionally, in this embodiment, the fixing base 5 includes a male fixing base 55 and a female fixing base 56. The male fixing base 55 and the female fixing base 56 are interconnected to form the whole fixing base 5. The male fixing base 55 and the female fixing base 56 are hinged at one end by a hinge shaft 57. A second groove 561 is provided on the other end of the female fixing base 56, a protrusion 551 is provided at the other end of the male fixing base 55, and the male fixing base 55 and the female fixing base 56 are connected by snap-fitting, with the protrusion 551 inserting into the second grove 561.

The second embodiment is an alternative of the first embodiment, with the difference in that the connecting base 6 is made of a fiberglass material, which has good insulation performance, strong heat resistance, high anti-corrosion effect, and high mechanical strength.

The third embodiment is an alternative of the first embodiment, with the difference in that the fixing base 5 is made of an electric ceramic material, which is a porcelain insulating material having good insulation performance and mechanical strength, excellent mechanical performance, good electrical performance, and high environmental resistance.

The fourth embodiment is an alternative of the first embodiment, with the difference in that the fixing ring 4 is made of a silicone rubber material, which has high-temperature stability, and able to maintain a certain degree of flexibility and elasticity in a high-temperature environment.

In the present disclosure, unless otherwise clearly specified and defined, when a first feature is described to be "on" or "under" a second feature, the first feature and the second feature may be in direct contact, or the first feature and the second feature may be in indirect contact by providing an intermediate structure therebetween.

Further, when a first feature is described to be "above" or "over" a second feature, the first feature may be right above or obliquely above the first feature, or it merely means that the level of the first feature is higher than that of the second feature. When a first feature is described to be "under" or "below" a second feature, the first feature may be right under or obliquely under the first feature, or it merely means that the level of the first feature is lower than that of the second feature.

In the description of the specification, the description with reference to the terms "one embodiment", "some embodiments", "examples", "specific examples" or "some examples", etc., means that specific features, structures, materials or characteristics described in connection with the embodiment or example are embraced in at least one embodiment or example of the present disclosure. In the specification, the illustrative expression of the above terms is not necessarily referring to the same embodiment or example. Moreover, the described specific features, structures, materials or characteristics may be combined in any suitable manners in one or more embodiments or examples. Furthermore, where no contradiction exists, the various embodiments or examples and features of various embodiments or examples described in this specification can be combined by those skilled in the art.

Finally, it should be noted that the above-described embodiments are merely illustrative of, and not intended to limit the technical solutions of the present disclosure. Although the present disclosure has been described in detail with reference to the foregoing embodiments, It should be understood by those of ordinary skill in the art that modifications can be made to technical solutions described in the foregoing embodiments, or equivalent replacements can be made to some or all of the technical features therein, without causing the essence of the corresponding technical solutions to deviate from the scope of the technical solution described in the embodiments of the present disclosure.

What is claimed is:

1. A radio-frequency ablation catheter, comprising a handle portion, a needle tube portion connected to a distal end of the handle portion, a central electrode for ablation treatment, and a detection mechanism, wherein the detection mechanism comprises:

a fixing base, a pulling string, a connecting base, and a plurality of detection electrodes arranged in a claw-shaped configuration, wherein the fixing base is provided with a plurality of mounting holes, and each of the detection electrodes extends through a respective mounting hole and is fixedly connected to the fixing base;

a distal end of the pulling string is fixed to the fixing base;

the connecting base is provided with a plurality of guide holes, each detection electrode extends through a respective guide hole, and the guide holes allow the detection electrodes to extend out of the connecting base in a dispersed manner; and each detection electrode comprises: a first section, a second section, and a third section, wherein an included angle between the second section and the first section is an obtuse angle, and an included angle between the third section and the second section is an obtuse angle, the needle tube portion comprises a first tube and a second tube, the handle portion comprises a cylinder sleeve and a sliding button, wherein the sliding button is slidably mounted on the cylinder sleeve, and a proximal end of the pulling string is fixed to the sliding button; and the central electrode comprises an electrode body, an electrode wire, and an electrode connector, wherein the electrode body, the second tube, the connecting base and the first tube are arranged in series in a direction from a distal end to a proximal end of the radio-frequency ablation catheter and fixedly connected one another, the electrode body is fixed to a distal end of the second tube and located at the distal end of the radio-frequency ablation catheter, the fixing base is slidably mounted in the first tube, and the plurality of detection electrodes are slidably located inside the first tube, a distal end of the electrode wire is electrically connected to the electrode body, the electrode wire extends through the cylinder sleeve, the first tube and the second tube, a proximal end of the electrode wire is electrically connected to the electrode connector, and the electrode connector is located outside the cylinder sleeve; and when the detection electrodes extend out of the connecting base in a dispersed manner, the detection electrodes are unfolded and surround the electrode body to obtain a temperature or impedance data of tissues around the electrode body of the central electrode so as to monitor progress of ablation of the central electrode, and distal ends of the detection electrodes are located on a same latitude.

2. The radio-frequency ablation catheter according to claim 1, further comprising a liquid injection joint and a liquid injection tube, wherein the liquid injection tube extends through the cylinder sleeve, the fixing base and the connecting base, the electrode body is provided with a liquid inlet, and a distal end of the liquid injection tube is communicated with the liquid inlet; and the liquid injection joint is provided at a proximal end of the liquid injection tube, and located outside the cylinder sleeve.

3. The radio-frequency ablation catheter according to claim 2, wherein the electrode body is provided with sprinkler channels therein, wherein the sprinkler channels are communicated with the liquid inlet, and the sprinkler channels are configured for dispersedly delivering the liquid at the liquid inlet.

4. The radio-frequency ablation catheter according to claim 3, wherein an infiltration cover is mounted around the electrode body with a gap formed therebetween, wherein the infiltration cover comprises a plurality of dispersing holes distributed in a rectangular array, and diameters of each row of dispersing holes decrease in a direction from a proximal end to a distal end.

5. The radio-frequency ablation catheter according to claim 4, wherein the electrode body comprises: a cylindrical portion and a tapered portion, wherein the tapered portion is located at a distal end of the cylindrical portion, and the infiltration cover is mounted around the cylindrical portion, surrounding an outer periphery of the cylindrical portion with the tapered portion exposed;

wherein the electrode body is provided with a temperature sensor and a signal conduit therein, and wherein a wiring hole is provided in the electrode body, wherein the temperature sensor is located in the tapered portion, the signal conduit extends through the wiring hole, an insulating layer is provided outside the signal conduit, a distal end of the signal conduit is electrically connected to the temperature sensor, and a proximal end of the signal conduit is electrically connected to the electrode connector.

6. The radio-frequency ablation catheter according to claim 1, wherein the connecting base comprises a liquid injection hole, wherein the liquid injection hole is positioned along a central axis of the connecting base, the liquid injection tube extends through the liquid injection hole, and the guide holes are symmetrically distributed with the liquid injection hole as a center; and each guide hole comprises a straight section and a curved section, wherein the curved section is located at a distal end of the straight section.

7. The radio-frequency ablation catheter according to claim 6, wherein each guide hole is provided with an anti-skid pattern on an inner side wall of the straight section thereof; or wherein each curved section is provided with an anti-wear pad on an inner side wall thereof, wherein the anti-wear pad is made of a rubber material.

8. The radio-frequency ablation catheter according to claim 6, wherein a mounting post is provided at a proximal end of the connecting base, and a spring is mounted around the mounting post, wherein when the fixing base moves towards the connecting base, a distal end of the spring abuts against the connecting base, and a proximal end of the spring abuts against the fixing base.

9. The radio-frequency ablation catheter according to claim 1, wherein the first section and the second section are both straight sections, and the third section is a curved section.

10. The radio-frequency ablation catheter according to claim 1, wherein two sides of the fixing base are provided with two first groove respectively, an another pulling string is provided, a distal end of each pulling string is provided with a fixture block, and the fixture block is fixedly engaged in a respective first groove, to allow the pulling strings and the fixing base to be fixedly connected.

11. The radio-frequency ablation catheter according to claim 1, wherein the fixing base comprises a female fixing base and a male fixing base interconnected to each other.

12. The radio-frequency ablation catheter according to claim 11, wherein the female fixing base and the male fixing base are hinged by a hinge shaft.

13. A radio frequency ablation system, comprising a radio-frequency ablation catheter according to claim 1.

14. An ablation method using the radio-frequency ablation catheter according to claim 1, comprising:

delivering the radio-frequency ablation catheter in a human body to a tissue to be ablated;

supplying a current to the central electrode to ablate the tissue by the central electrode; and moving the fixing base distally to push the detection electrodes out of the first tube such that the plurality of detection electrodes surround the electrode body of the central electrode to detect a temperature or an impedance of the tissue around the electrode body of the central electrode.

15. The radio-frequency ablation catheter according to claim 1, further comprising a plurality of fixing rings, wherein a distal end of each fixing ring is fixed to a respective detection electrode, and a proximal end of each fixing ring is externally connected to a wire, allowing the wire and the respective detection electrode to be electrically connected.

16. The radio-frequency ablation catheter according to claim 15, wherein the fixing rings and the fixing base are connected by interference fit to limit lengths of the detection electrodes protruding out.

17. The radio-frequency ablation catheter according to claim 15, wherein each fixing ring is a hollow cylinder, and each fixing ring is provided with a slit.

18. The radio-frequency ablation catheter according to claim 15, wherein two ends of each fixing ring are each provided with a buffering cushion.

19. The radio-frequency ablation catheter according to claim 1, wherein the second tube is provided with an internal thread at a proximal end thereof, the connecting base is provided with an external thread at the distal end thereof, and the connecting base and the second tube are threadedly connected.

20. The radio-frequency ablation catheter according to claim 1, wherein the connecting base is provided with a threaded hole at the proximal end thereof, the first tube is provided with a counterbore at a distal end thereof, and a bolt is inserted into the counterbore and the threaded hole to fix the connecting base and the first tube together.

21. The radio-frequency ablation catheter according to claim 20, wherein the connecting base has a first cylindrical section and a second cylindrical section connected with each other along the direction from the distal end to the proximal end of the radio-frequency ablation catheter, the first cylindrical section has a diameter greater than the second cylindrical section, the threaded hole is provided on an outer periphery of the second section, the guide holes extend from a proximal end surface of the second cylindrical second into the first cylindrical section and out of the first cylindrical section from an outer periphery of the first cylindrical section.

* * * * *